(12) United States Patent
Pens et al.

(10) Patent No.: US 11,517,373 B2
(45) Date of Patent: Dec. 6, 2022

(54) SWITCHED LASERS FOR DERMAL TREATMENT

(71) Applicant: Alma Lasers Ltd., Caesarea (IL)

(72) Inventors: Yevgeny Pens, Kiryat Bialik (IL); Gabi Godelman, Kiryat Motzkin (IL); Ziv Karni, Kfar Shmaryahu (IL)

(*) Notice: Subject to any disclaimer, the term of this patent is extended or adjusted under 35 U.S.C. 154(b) by 271 days.

(21) Appl. No.: 15/854,859

(22) Filed: Dec. 27, 2017

(65) Prior Publication Data

US 2018/0177551 A1 Jun. 28, 2018

Related U.S. Application Data

(60) Provisional application No. 62/439,158, filed on Dec. 27, 2016.

(51) Int. Cl.
| | |
|---|---|
| *A61B 18/20* | (2006.01) |
| *H01S 5/40* | (2006.01) |
| *H01S 5/042* | (2006.01) |
| *A61B 18/00* | (2006.01) |
| *A61N 5/06* | (2006.01) |
| *A61N 5/067* | (2006.01) |

(52) U.S. Cl.
CPC .......... *A61B 18/203* (2013.01); *H01S 5/0428* (2013.01); *H01S 5/4025* (2013.01); *A61B 2018/00005* (2013.01); *A61B 2018/00047* (2013.01); *A61B 2018/00452* (2013.01); *A61B 2018/00476* (2013.01); *A61B 2018/00708* (2013.01); *A61B 2018/20553* (2017.05); *A61N 5/067* (2021.08); *A61N 5/0616* (2013.01)

(58) Field of Classification Search
CPC ....... A61B 18/18; A61B 18/20; A61B 18/203; A61B 2018/2035; A61B 2018/2553; A61B 18/22; A61B 2018/2255; A61B 2018/2266; A61B 2018/00005; A61B 2018/00452; A61B 2018/0047; A61B 2018/00476; A61B 2018/00696; A61B 2018/00702; A61B 2018/00708; A61N 5/06; A61N 5/0613; A61N 5/0616; A61N 2005/0626; A61N 2005/0642; A61N 2005/0643; A61N 2005/0644; A61N 2005/0659; A61N 2005/067; H01S 5/40; H01S 5/4025
USPC .............. 606/3, 9–13, 16–19; 607/88–91, 93
See application file for complete search history.

(56) References Cited

U.S. PATENT DOCUMENTS

| | | | | |
|---|---|---|---|---|
| 3,568,087 | A * | 3/1971 | Phelan, Jr. ................ | H01S 5/30 372/68 |
| 4,862,888 | A * | 9/1989 | Yessik ..................... | A61F 9/008 606/4 |
| 6,015,404 | A * | 1/2000 | Altshuler ............. | A61B 18/203 606/10 |
| 6,579,283 | B1 * | 6/2003 | Tobinick .............. | A61B 18/203 606/10 |

(Continued)

*Primary Examiner* — Ahmed M Farah
(74) *Attorney, Agent, or Firm* — Clifford D. Hyra; Aubrey Y. Chen; Richard Jaffe

(57) ABSTRACT

An applicator comprising multiple laser assemblies connected to a power supply and a controller that switches each pulse to a different one of the laser assemblies. Each laser assembly deposits a laser spot on the skin and the result is to produce a large 'aggregate' spot without requiring extra power or extra lasers. In one embodiment, each pulse serves as a trigger to switch the next pulse to the next laser assembly.

12 Claims, 4 Drawing Sheets

(56) References Cited

U.S. PATENT DOCUMENTS

| | | | | |
|---|---|---|---|---|
| 6,595,985 B1 * | 7/2003 | Tobinick | A61B 18/203 | 606/13 |
| 7,427,289 B2 | 9/2008 | Sierra et al. | | |
| 7,762,965 B2 * | 7/2010 | Slatkine | A61B 18/203 | 601/7 |
| 8,286,643 B2 * | 10/2012 | Li | A45D 29/00 | 132/73 |
| 10,471,274 B2 | 11/2019 | Liu et al. | | |
| 2002/0002391 A1 * | 1/2002 | Gerdes | A61N 5/0616 | 607/89 |
| 2005/0075703 A1 * | 4/2005 | Larsen | A61N 5/062 | 607/88 |
| 2008/0077198 A1 * | 3/2008 | Webb | A61N 5/0618 | 607/88 |
| 2008/0119831 A1 * | 5/2008 | Myeong | A61N 5/0613 | 606/13 |
| 2009/0234343 A1 * | 9/2009 | Behrakis | A61B 18/203 | 606/9 |
| 2009/0254068 A1 * | 10/2009 | Karni | A61B 18/203 | 606/3 |
| 2012/0010684 A1 * | 1/2012 | Owens | A61B 18/203 | 607/88 |
| 2012/0226268 A1 | 9/2012 | Liu et al. | | |
| 2013/0030421 A1 * | 1/2013 | Gomez De Diego | A61N 5/0616 | 606/3 |
| 2013/0150841 A1 * | 6/2013 | Schomacker | A61B 18/203 | 606/13 |
| 2014/0081359 A1 * | 3/2014 | Sand | A61N 5/0613 | 607/90 |
| 2014/0155876 A1 * | 6/2014 | Grove | A61B 18/203 | 606/9 |
| 2014/0214136 A1 | 7/2014 | Liu et al. | | |
| 2015/0127075 A1 * | 5/2015 | Ward | A61N 5/0616 | 607/90 |
| 2015/0246242 A1 * | 9/2015 | Delp | A61N 5/0622 | 604/20 |

* cited by examiner

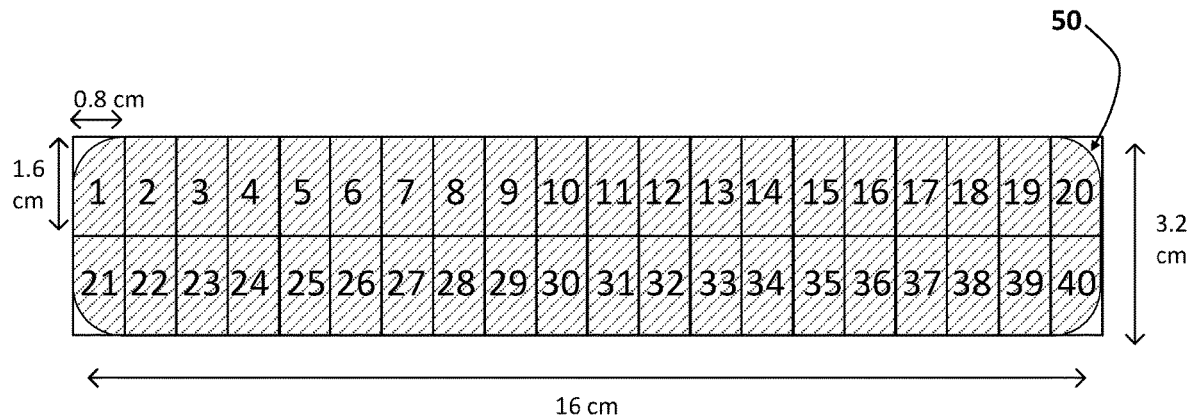
FIGURE 1 – PRIOR ART
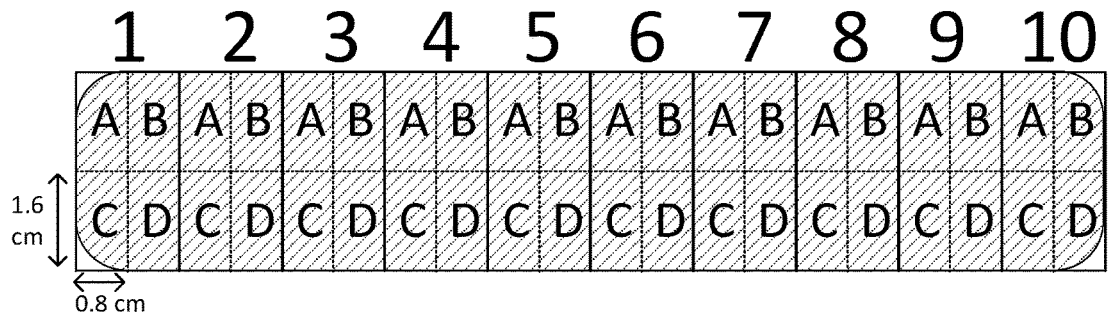
FIGURE 2

SWITCHED LASERS FOR DERMAL TREATMENT

RELATED APPLICATION

The present application claims the benefit of U.S. Provisional Patent Application No. 62/439,158 filed Dec. 27, 2016, the disclosure of which is incorporated herein by reference in its entirety.

BACKGROUND

The present invention concerns lasers applied to a person's skin to effect aesthetic improvement or medical treatment. Some uses include treatment of acne, tightening of wrinkles, tissue remodeling, and removal of hair. The invention can also be used on other mammalian skin.

In laser hair removal, a laser beam applied to an area of skin surface penetrates to the dermal layer where it thermally damages target structures in or near the hair follicles. The wavelength of the laser beam is selected for absorption by chromophores found in relative high concentration in the target structures and relatively low concentration in the skin surface and intervening tissue, so that most of the beam passes through to be absorbed in the target structures. A popular wavelength for laser hair removal is 810 nm (nominal), which is highly absorbed by melanin, a chromophore found in hair roots, particularly darker hair roots. As different wavelengths have different penetration and absorption characteristics, in some cases multiple wavelengths are applied. For example, with the goal of increasing the volume of tissue treated or reducing energy lost to surface absorption. Popular wavelengths for such combined application are 755 nm, 810 nm, and 1064 nm (all nominal).

The laser is applied from an applicator, usually handheld, which is brought into contact with a target area of skin. Semiconductor lasers, particularly laser diodes, are popular for their relative electrical efficiency, low cost of ownership, and small size to fit inside the applicator. In professional devices, the applicator is connected via an "umbilical" cable to a console containing a user interface for setting system parameters, a power supply for powering the diode lasers, and a heat exchanger for cooling applicator components. In home use devices, the applicator is a standalone format with onboard controls, cooling, and a rechargeable battery.

High power diode lasers are implemented as a row of about 10 to 50 side-by-side emitters integrated into a single chip, or bar. Even more power is obtained by mounting about 10 to 20 bars in a stack to form a two-dimensional array of lasers. In some cases multiple stacks are used. In some devices, the laser beams radiate directly onto the skin, in others, they pass first through optics. The area of skin on which the beams are incident is referred to as the laser spot.

Spot Size

Depending on the desired amount of fluence to deposit, one or more pulses of laser energy can be applied to the spot. Most treatment areas, for example the chest, are larger than the spot, so the applicator is applied in a series of steps: it is set on a first location on the skin and activated to deposit a first spot, then moved ('stepped') to an adjoining location and activated to deposit a second spot adjoining the first spot, then stepped to a next adjoining location and so forth until the deposited spots cover the entire treatment area. In some applications, instead of such step-and-fire operation, the applicator is swept back and forth across the treatment area with the laser activated continuously until a desired average fluence has been deposited across the treatment area.

The power (watts=joules per second) of the diode laser beams times the length of time (s) in which they are applied determines the amount of energy (J) deposited by the beams at the spot. The energy (J) divided by the area of the spot (cm^2) determines the amount of fluence (F), or radiant energy per unit area, deposited (J/cm^2). For a given quantity of energy, the larger the spot, the less fluence.

Stepping the applicator across the treatment area is time consuming and when done manually, fatiguing. A common spot size is about 1 cm by 1 cm. To cover a treatment area of 10 cm by 30 cm, or 300 square cm, requires 300 steps of the applicator. In addition to the lengthy treatment time and operator fatigue, there is the risk of unequal application due to misaligned spots.

In some treatments, the goal is to completely cover the treatment area by applying adjoining spots. The meaning of the word 'adjoin' as used in this specification is 'to be close to or in contact with one another'. But each time the applicator is stepped, there is a possibility of unintentional misalignment, resulting in an untreated gap between non-contiguous spots or an overheated region of overlapped spots.

A larger spot size is therefore desirable, but there are limitations. By definition, the fluence (energy per unit area) drops with the increase in spot size (area of incidence). To maintain the fluence level while depositing a larger spot requires a higher supply voltage and more laser diodes. These are expensive and there is a greater likelihood of injury or pain for the person who is the subject of the treatment.

Attempts have been made to compensate for the lower fluence engendered by a larger spot size. The Lightsheer Duet HS applicator manufactured by Lumenis Ltd. of Israel has a 7.7 square cm spot. Suction stretches the skin up into a gold-plated concave chamber. The stretching separates the epidermal chromophores, so less energy is lost to them, and constricts vessels, so there is less oxyhemoglobin to compete as a chromophore. The gold plates redirect otherwise lost reflected energy back to the skin. It is not certain to what degree these additions compensate for lower fluence and they add to cost and complexity.

BRIEF SUMMARY

In the present invention devices, systems, and methods are provided in which a laser applicator comprising two or more laser assemblies is arranged to apply adjoining spots when activated over a patient's skin. Pulses from a power source are switched to each laser assembly in sequence, resulting in multiple adjoining spots deposited on the skin. The effect is to produce an 'aggregate' spot as large as the total areas of the individual spots and to do so without requiring a separate power source for each laser assembly.

In some embodiments, the controller comprises switching is incremented by an internal trigger, for example, the voltage or current of the pulse or the light produced.

In some embodiments, the counter comprises outputs, each of which is connected to the gate of a transistor connected to a laser assembly, wherein activation of the output puts the transistor into an 'on' state, switching the next pulse to that laser assembly.

In some embodiments, the laser assemblies may be arranged in one or more of three ways: so that their respective spots adjoin, overlap in part or in full, or neither adjoin nor overlap.

In some embodiments, the laser assembly comprises semiconductor lasers, such as stacks of bars of laser diodes. In some embodiments, each stack is associated with a cylindrical lens.

In some embodiments, some of the laser assemblies are of different wavelengths from one another. In some embodiments, the wavelength of the laser energy produced by the laser assembly is between 755 nm +/−20% and 1064 nm +/−20%.

In some embodiments, the laser assemblies are associated with a cooled window that is applied against the skin.

Various objects, features, aspects, and advantages of the present invention will become more apparent from the following detailed description of preferred embodiments of the invention, along with the accompanying drawings in which like numerals represent like components".

BRIEF DESCRIPTION OF THE DRAWINGS

FIG. 1 illustrates results of applying a prior art laser applicator to an area of a subject's skin FIG. 2 illustrates results produced by a laser applicator constructed in accordance with the present invention to an area of a subject's skin comparable to that in FIG. 1.

DETAILED DESCRIPTION

The present invention is directed to switching pulsed power between multiple laser assemblies to treat a subject's skin. In this manner a single power supply can supply all the laser assemblies, by supplying one at a time.

The subject can be a human or other mammal. The application can be medical or cosmetic.

In some embodiments, the laser assemblies are arranged so that the individual laser spots produced on the skin by their incident beams adjoin one another to form a relatively large aggregate laser spot. In other embodiments, the laser assemblies are arranged so that the individual laser spots uniformly overlap (i.e., are coincident) in part or in full. In other embodiments, the laser assemblies are arranged so that the individual laser spots are spaced apart by regular regions of skin that remain untreated.

FIG. 1 illustrates results of a prior art device used to treat a skin surface area 50 measuring about 3.2 cm by 16 cm, or about 51 square cm. The spot size of the prior art device is about 0.8 cm by 1.6 cm, or 1.28 square cm, so 40 steps are required to cover the target skin area.

FIG. 2 illustrates results obtained on the same skin area by an embodiment of the invention comprising four laser assemblies. Each laser assembly has a spot size like that of the prior art device, about 0.8 cm by 1.6 cm, or 1.28 square cm. After each step (advance) of the applicator, power is switched sequentially to each of the four laser assemblies, to produce a set of adjoining spots (labeled A, B, C, and D) forming an 'aggregate spot' of 4×1.28 square cm, or 5.12 square cm. In ten steps, labeled 1 to 10, the target area is covered. The switching sequence can hardwired or set by the operator, for example through a graphical user interface. The switching sequence can be any number of activations of a given laser assembly, any order in which the laser assemblies are activated, and any number of repetitions of the switching sequence. Some examples: one activation of the laser assembly incident on spot A, then the one of the laser assembly incident on spot B, then one of the assembly incident on spot C, and then one of the assembly incident on spot D. Or multiple activations of each laser assembly before switching to the next laser assembly. Or different numbers of activations depending on the laser assembly. Or a round of single or multiple activations of each laser assembly followed by more rounds.

In the example, the invention requires 75% less steps than the prior art. Treatment is accordingly much faster with less operator effort and less risk of faulty alignment.

Figure 3:
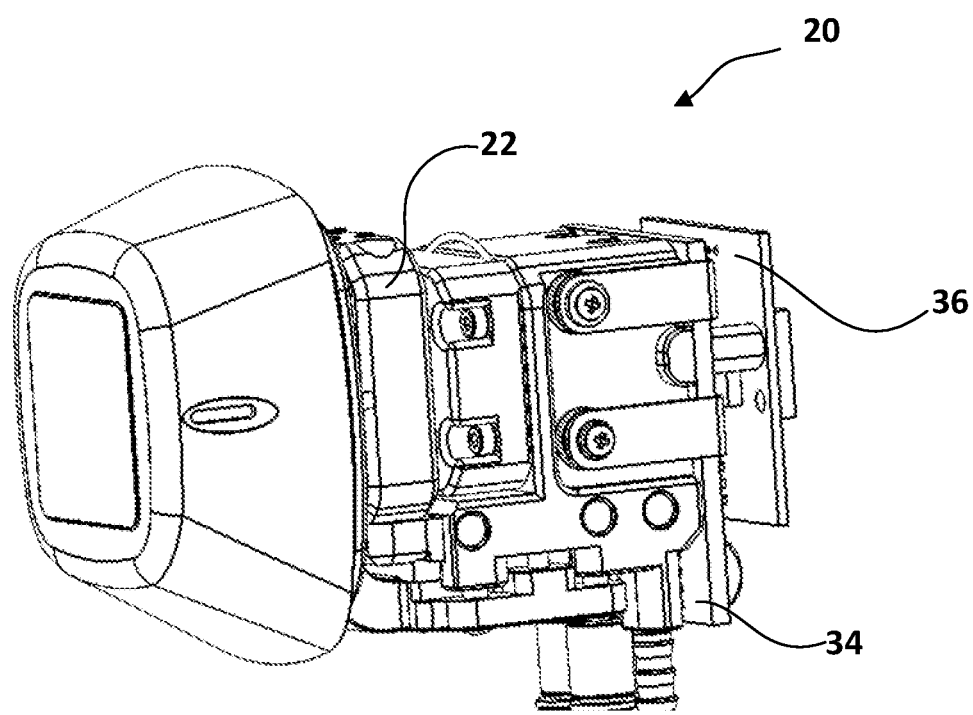
FIG. 3 is a view of components of a laser applicator constructed in accordance with the present invention.
Figure 4:
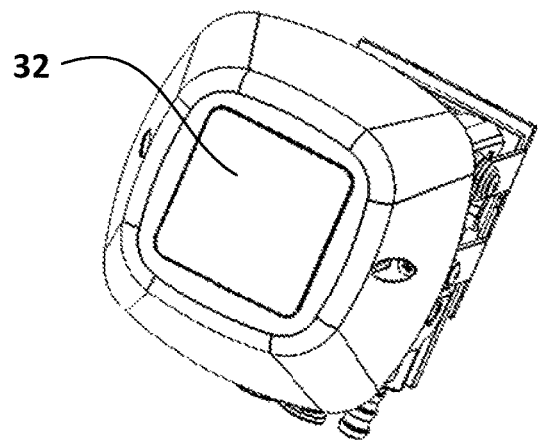
FIG. 4 is a view of a treatment of window of the applicator of FIG. 3.
Figure 5:
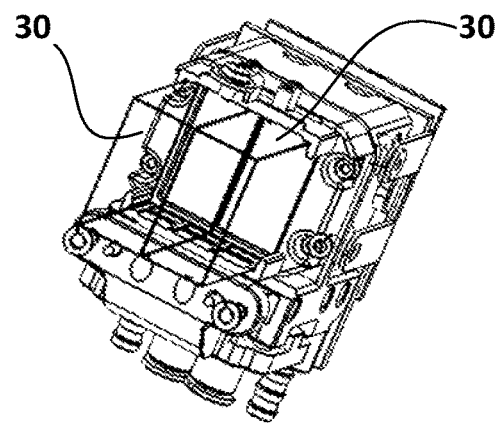
FIG. 5 is a view of parts of a laser assembly in the applicator of FIG. 3.
Figure 6:
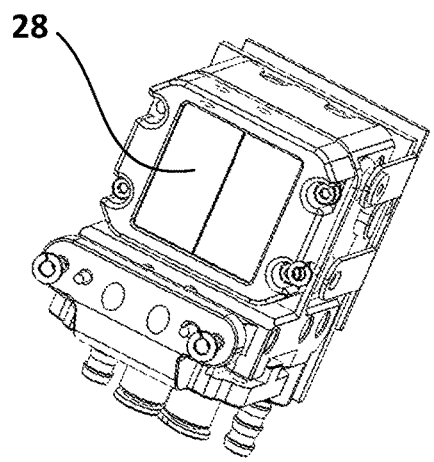
FIG. 6 is a view of lenses of a laser assembly in the applicator of FIG. 3.
Figure 7:
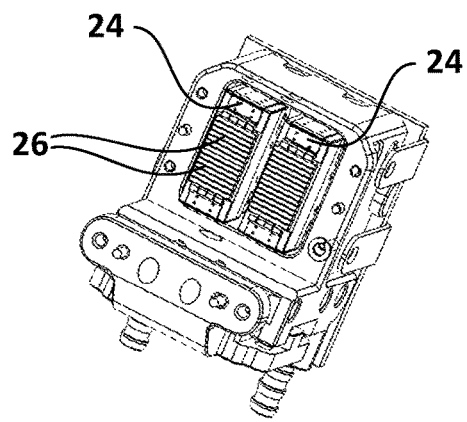
FIG. 7 is a view of other parts of a laser assembly in the applicator of FIG. 3.

FIG. 3 depicts a laser treatment applicator 20 in accordance with an embodiment of the invention. The applicator shown is handheld with the outer shell removed. Automated embodiments are also possible. Pulses from a diode driver (not shown) are supplied through an umbilical cord (not shown) and routed sequentially by controller 34 through switches 36 to laser assemblies 22. In some embodiments, applicator 20 is a standalone device, for example in home use formats.

FIGS. 4 to 7 show components of laser assembly 22. There are at least two laser assemblies 22, each comprising a laser diode stack 24. Laser diode stack 24 is optically associated with a plano concave cylinder lens 28, which is optically associated with a light guide 30. Light guides 30 are optically associated with a cooling window 32.

In use, pulses from the diode driver are switched sequentially to laser diode stacks 24 where they are converted into laser output beams that are widened along their slow axis by lens 24, then are channeled and shaped by light guide 30, and then pass through laser-transparent window 32, which is in contact with the subject's skin, to deposit a spot of laser energy on the skin. Window 32 is chilled by a thermoelectric cooler and so cools the skin surface by conduction. Laser assembly 22 is radiatively cooled by a circulating coolant.

In some embodiments the spot size produced is about 16 mm by 8 mm. However other common sizes may be used.

Figure 8:
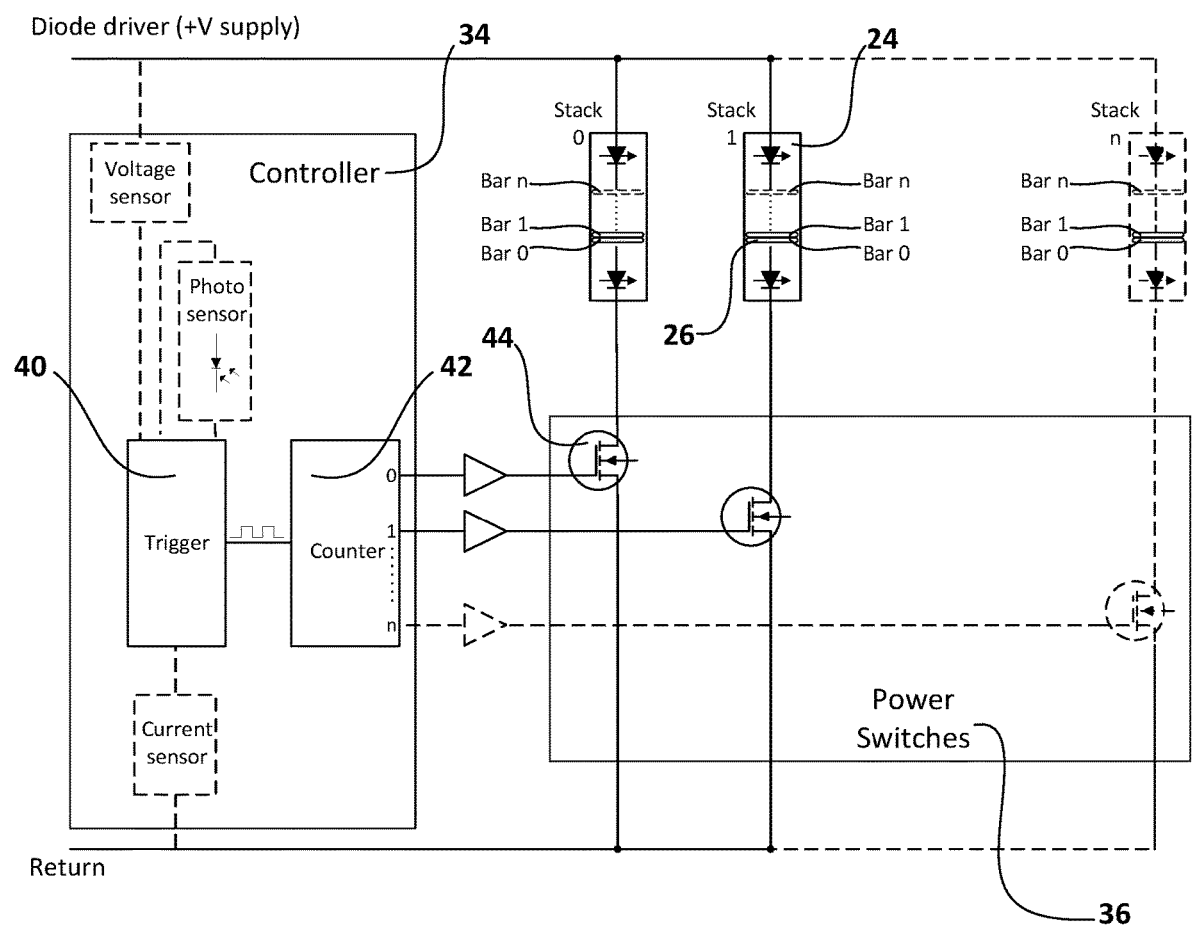
FIG. 8 is a block diagram and simplified circuit diagram of a laser applicator constructed in accordance with the present invention.

There are many ways to switch the pulses between the diode laser stacks 22. FIG. 8 shows an embodiment with automatic switching to route a pulse sequentially to each diode stack 24.

Each activation of trigger 40 increments counter 42, activating a different output, which puts a signal on the gate of an associated transistor 44, which acts as a low side switch, opening the path between the drain and the source for a pulse to reach the associated diode laser array 24.

An internal trigger detects the event. For example, the trigger might be detection of the change in pulse voltage or current or it might be detection of the laser light. The trigger detection is performed off-line (not under load) for increased reliability and decreased switching losses in the circuit.

In some embodiments, the controller can be an external component, such as a microcontroller. In such cases, the controller can be programmed to switch on the transistor for a number of pulses or it can be programmed to repeat the switching sequence a number of times.

The embodiment shown in FIGS. 3 to 7 comprises two laser assemblies 22. Alternatively, there can be 3, 4, 5, 6, 7, 8, 9, 10 or even more laser assemblies within practical limits, such as weight limitations. Similarly, each diode laser stack 24 can comprise any practical number of diode laser bars 26. In some embodiments, there may be more than one diode laser stack 24 per diode laser assembly 22.

Laser diode stacks 24 may be all of a single wavelength or some or all of them may be of different wavelengths. The laser diode bars 26 of a laser diode stack 24 may be all of a single wavelength or some or all may be of different wavelengths.

The arrangement of the laser assemblies 22 in applicator 20 depends on the desired spot pattern. In some embodiments, the laser assemblies 22 are arranged so that the spots produced at least substantially adjoin one another to form an aggregate spot of maximum size.

In some other embodiments, at least some laser assemblies 22 may be arranged so that the spots produced overlap in whole (i.e., cover the same specific area) or in part. For example, laser assemblies of different wavelengths could be arranged to treat the same spot. While the aggregate spot size would be smaller, there is the benefit of applying multiple wavelengths at full fluence without having to move the applicator.

In some embodiments, at least some laser assemblies 22 may be arranged with a gaps between them, for example to create lines of undamaged skin to accelerate post-treatment recovery from thermal damage to the treated parts of the skin surface.

In some embodiments, applicator 20 is a stationary device. In some embodiments, there are multiple instances of applicator 20. For example, a number of applicators 20 may be positioned at different locations on the target skin area and applied concurrently.

What is claimed is:

1. A device for applying laser energy to human or other mammalian skin, the device comprising:
    at least one applicator, each applicator comprising two or more laser assemblies, each laser assembly configured to receive an electrical pulse and convert it into laser energy incident on a spot of the skin;
    a controller configured to switch an electrical pulse or a group of electrical pulses to each laser assembly in sequence;
    wherein the controller comprises a counter incremented by an internal trigger, wherein the internal trigger detects an event selected from the group consisting of a change in pulse voltage, a change in pulse current, a change in laser energy intensity, and combinations thereof.

2. The device of claim 1 wherein the laser assemblies are arranged so that the distribution of their respective deposited spots is selected from at least one of the group consisting of adjoining, overlapping in full and not adjoining.

3. The device of claim 1 wherein the controller is configured to switch multiple pulses to each laser assembly in sequence.

4. The device of claim 1 wherein the controller is configured to repeat the switching multiple times.

5. The device of claim 1 wherein the counter comprises outputs, each output connected to the gate of a transistor, each transistor connected to a laser assembly, wherein activation of the output puts the connected transistor into an 'on' state, switching the next pulse to the connected laser assembly.

6. The device of claim 1 wherein the laser assembly comprises a semiconductor laser.

7. The device of claim 6 wherein the semiconductor laser comprises a stack of bars of laser diodes.

8. The device of claim 7 wherein each laser assembly is associated with at least one from the group consisting of a cylindrical lens and a light guide.

9. The device of claim 1 wherein at least some laser assemblies are of different wavelengths from one another.

10. The device of claim 1 wherein the wavelength of the laser energy produced by the laser assembly is between 755 nm +/−20% and 1064 nm +/−20%.

11. The device of claim 1 further comprising a cooled window.

12. The device of claim 1 wherein the counter comprises outputs, each output connected to the gate of a transistor, each transistor connected to a laser assembly, wherein activation of the output puts the connected transistor into an 'on' state, switching the next pulse to the connected laser assembly.

* * * * *